United States Patent [19]

Panico

[11] 4,203,451
[45] May 20, 1980

[54] CARDIOVASCULAR ANALYSIS, METHOD AND APPARATUS

[76] Inventor: Joseph J. Panico, 8 Farrington St., Arlington, Mass. 02174

[21] Appl. No.: 887,505

[22] Filed: Mar. 17, 1978

[51] Int. Cl.² .............................................. A61B 5/02
[52] U.S. Cl. ................................................... 128/672
[58] Field of Search ...................... 128/2.05 A, 2.05 F, 128/2.05 Q, 2.05 P, 2.05 R, 2.05 V, 2.06 R

[56] References Cited

U.S. PATENT DOCUMENTS

| | | | |
|---|---|---|---|
| 3,773,033 | 11/1973 | Rodbard et al. | 128/2.05 P |
| 3,831,590 | 8/1974 | Boyle et al. | 128/2.05 R |
| 3,841,313 | 10/1974 | Wesseling et al. | 128/2.05 V |
| 3,908,639 | 9/1975 | McIntyre | 128/2.05 R |
| 3,920,004 | 11/1975 | Nakayama | 128/2.05 P |

OTHER PUBLICATIONS

Rodbard et al., "Review of Scientific Instruments", vol. 32, No. 9, Sep. 1951, pp. 1022–1023.

*Primary Examiner*—William E. Kamm
*Attorney, Agent, or Firm*—Thomas N. Tarrant

[57] ABSTRACT

Left ventricular end diastolic pressure is determined by data processing analysis of EKG waveform, first heart sound and carotid pulse waveform. Electrical, sonic and pressure transducers obtain patient data noninvasively and provide it to a data processing system.

9 Claims, 5 Drawing Figures

CARDIOVASCULAR ANALYSIS, METHOD AND APPARATUS

BACKGROUND OF THE INVENTION

1. Field of the Invention

The present invention relates to cardiovascular analysis and in particular to the determination of left ventricular end diastolic pressure (LVEDP) for such analysis.

2. Description of the Prior Art

With lengthening life spans, cardiovascular malfunction has become an increasingly major cause of invalidism and death. Pulse rate, blood pressure and the electrical impulses of the heart are now commonly included in physical checkups using well known noninvasive techniques.

While a lot can be determined using the above techniques, other information has frequently been found desirable in cardiovascular analysis. This has led to the use of invasive techniques using catheters, fluid injection, X-rays and ultrasound. Invasive techniques are used to obtain the key parameters of cardiac output, stroke volume systemic resistance and left ventricular end diastolic pressure. Of these parameters, some experts consider left ventricular end diastolic pressure a significant and consistent indicator of cardiac function.

SUMMARY OF THE INVENTION

The present invention provides a noninvasive method for determining LVEDP by detecting and processing electrocardiograph (EKG) signals, heart sound signals, carotid pressure signals and diastolic pressure. The carotid pressure signal closely approximates the aortic pressure signal when there are no valvular or arterial defects present. The EKG, heart sound and carotid pressure signals are processed to obtain time references, carotid pressure signal is further processed to obtain the carotid pressure curve slope near the beginning of its rise systolic and, diastolic pressure is detected and all of these are processed together in accordance with the equation:

$$LVEDP = DIA - (T3 - T2)CS$$

Where:

DIA = Diastolic pressure such as obtained from a sphygmomanometer.

T3 = Time from start of EKG QRS complex to start of carotid pressure upstroke.

T2 = Time from start of QRS complex to start of first heart sound.

CS = Slope at beginning of carotid pressure curve.

Apparatus takes the form of EKG transducers, sonic heart sound transducer, neck pressure transducer for sensing carotid artery pressure, electronic circuitry for processing the signals from these transducers, a sphygmomanometer for obtaining systolic and diastolic pressure, and data processing equipment for receiving and processing all of this data in accordance with the above equation.

DESCRIPTION OF THE PREFERRED EMBODIMENT

Figure 1:
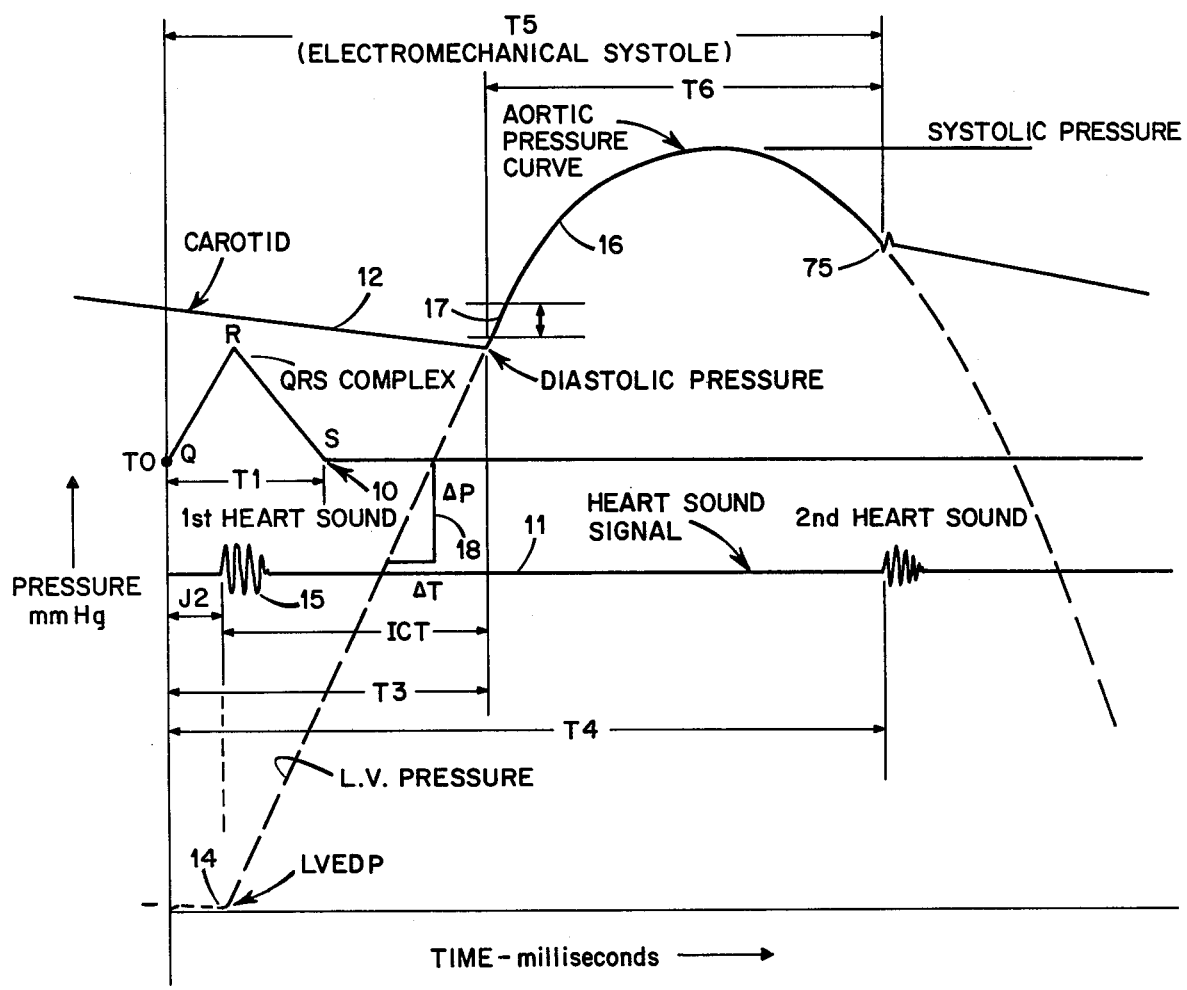
FIG. 1—Graphical representation of a cardiac cycle.

The method for obtaining LVEDP requires the acquisition of key cardiac parameters including the waveforms for QRS complex 10, heart sounds 11 and carotid pulse pressure 12 as shown in FIG. 1. Additionally, systolic (SYS) and diastolic (DIA) brachial artery cuff pressure must be determined. Either right or left cuff pressure may be used, but left is usually closer to the heart and is thus preferred. The techniques for the acquisition of these parameters are, in general, well known in the art. The time relationships among these parameters are shown in the waveforms of FIG. 1. All of these signals are obtained using appropriate transducers properly placed on the body of the patient as described more fully in apparatus.

Left ventricular end diastolic pressure 14 is the pressure existing in the left ventricular chamber at the end of diastole or the very beginning of systole, and is well understood by those versed in the art. Just prior to closing of the mitral valve (located between the left ventricle and the left atrium) and coincident with the start of the first heart sound in the normal heart, the left ventricular pressure is lowest. Referring to FIG. 1, the time from the start (T0) of QRS complex 10 to the beginning (T2) of first heart sound 15 identifies the time point, during the Cardiac Cycle, using the beginning of the QRS complex as the reference point, at which the left ventricular pressure is at its lowest point and starts to increase. It is this pressure that is determined noninvasively by the present method.

To determine LVEDP, it is necessary to obtain the signals shown in FIG. 1, determine the time relationship between the beginning (T0) of QRS complex 10, and the beginning (T2) of first heart sound 15 and the time relationship between T0 and the beginning (T3) of pressure pulse 16 (also carotid pulse), a time equivalent to the beginning of the carotid pulse (neck artery). It is also necessary to determine, using a standard pressure cuff or similar means, the systolic and diastolic pressure in a brachial artery close to the aorta and carotid arteries. The cuff pressure so obtained is used to calibrate the transducer used to obtain carotid pulse pressure 12.

The brachial artery in the upper left arm and the carotid artery in the neck are closely connected to the aorta and thus exhibit a highly similar pressure curve, slightly delayed in time. The aorta, being the primary distributing artery from the heart, follows the left ventricular pressure very closely after the aortic valve opens. Thus, it is possible to obtain a calibrating pressure reference from a cuff sensing the brachial artery and to obtain relative variations by a sensor sensing the carotid artery all indicative of left ventricle pressure change.

In addition to the above information, it is necessary to determine, by signal processing means, slope 17 of carotid pulse pressure 12 at the beginning (T3) of the carotid pulse as shown in FIG. 1, points A and B. Slope 17 is taken to be equal to left ventricular pressure slope 18 prior to the opening of the aortic valve (diastolic pressure point).

LVEDP is then computed using the formula:

$$LVEDP = DIA - (T3 - T2)CS$$

Where:

DIA = Cuff diastolic pressure.
T3 = Time from start of QRS complex to start of carotid pulse.
T2 = Time from start of QRS complex to start of first heart sound.
CS = The pressure/time slope 17 of the carotid pulse at the beginning of the carotid pulse.

In practice it is important to note that since the cuff diastolic pressure may vary somewhat over a short interval of time, several measurements should be made to maintain calibration and to be assured that a proper determination of LVEDP is obtained.

The method thus consists of:

1. Detecting the start of the QRS complex in an EKG signal;
2. Detecting the following first heart sound and measuring the time lapse following the start of the QRS complex;
3. Detecting the start of the carotid artery pressure pulse and measuring the time lapse following the start of the QRS complex;
4. Measuring the rate of pressure rise with time in the carotid artery immediately following the preinjection period (T3); and
5. Processing the data obtained in the preceding steps in accordance with the equation:

$$LVEDP = DIA - (T3 - T2)CS$$

Because of variations from beat to beat, optimum results are obtained if the results of several succeeding cycles are averaged.

Further method details are given in the following description of apparatus and its operation.

Figures 2, 2A:
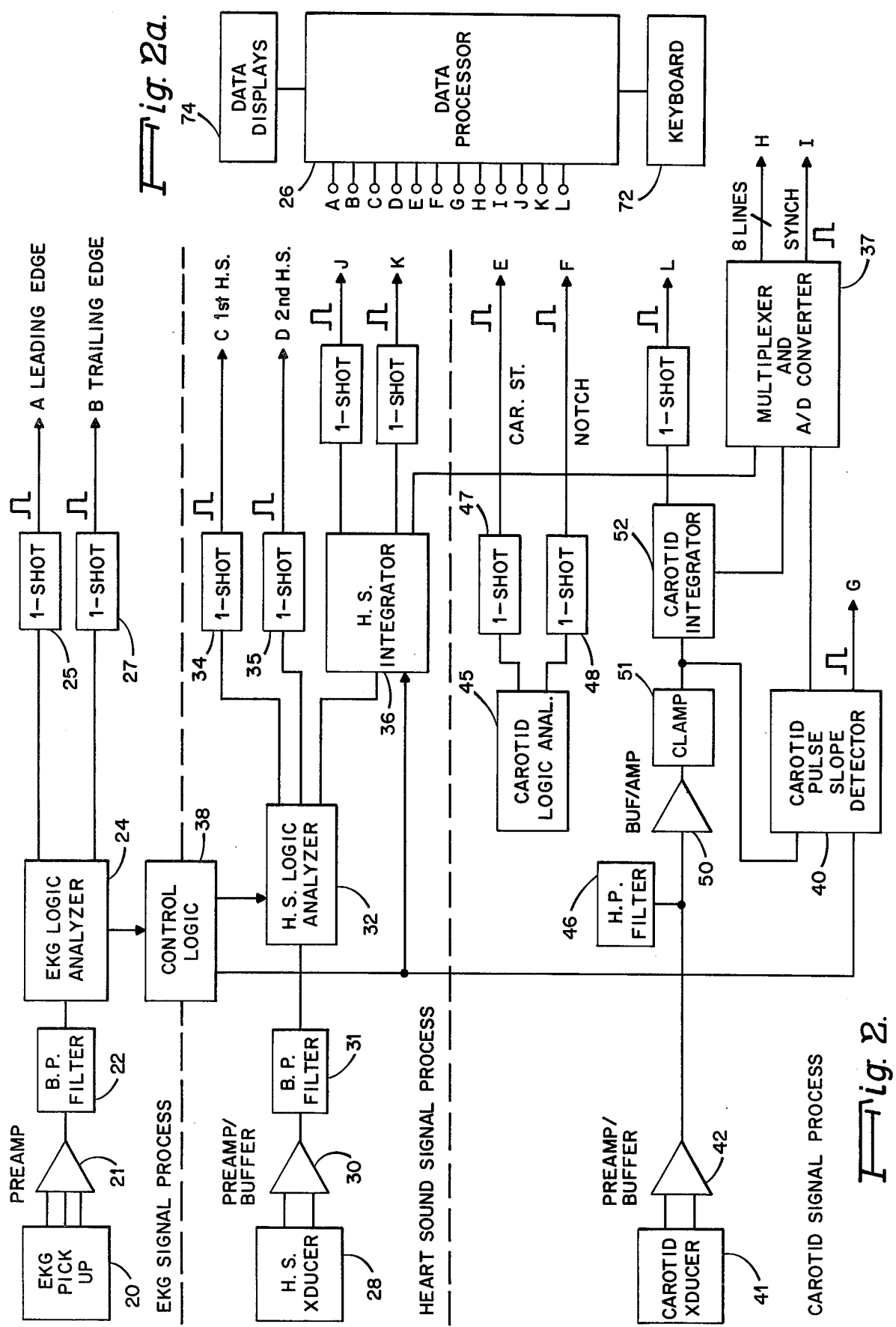
FIG. 2—Block Diagram of a cardiac analyzer in accordance with the invention.
FIG. 2a—Block diagram of data processor.

A block diagram of the system for measuring and displaying cardiac data and determining key parameters such as LVEDP is shown in FIG. 2. A diagram showing the placement of the EKG electrodes and the heart sound and carotid transducers is shown in FIG. 3.

Referring to FIG. 2, the EKG signal process section consists of set 20 of two or three EKG electrodes, high impedance differential preamplifier 21, bandpass filter network 22 and EKG logic analyzer 24. Preamp 21 and filter network 22 condition the EKG signal obtained from the patient via set 20 prior to application to logic analyzer 24. Logic analyzer 24 consists of a network of gates and one-shot multivibrators which determine the leading edge time and the trailing edge time of QRS complex 10. The leading edge is identified as T0, the beginning of the cardiac cycle. This signal is then fed to one-shot multivibrator 25, the output of which is connected to data processor 26 as signal A. Trailing edge time signal, T1, is also fed to one-shot multivibrator 27, the output of which is connected to processor 26 as signal B.

Figure 3:
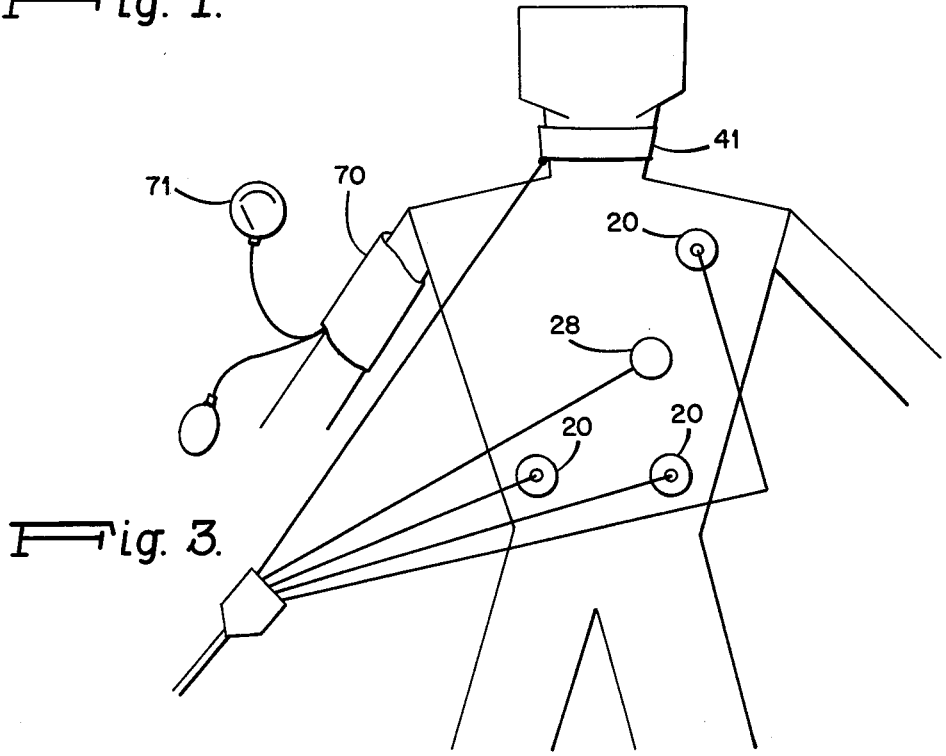
FIG. 3—Diagrammatic view of sensor locations on a human body for detecting signals according to the invention.

The heart sounds are processed in a similar manner, as shown in FIGS. 2 and 3. Heart Sound transducer 28, located on the patient's chest near the apex of the heart, is connected to buffer/preamp 30 which in turn is connected to bandpass filter network 31. Filter network 31 is connected to heart sound logic analyzer 32. Analyzer 32 consists of a network of gares and one shots for determining the times of the beginning of the first Heart Sound, T2, and beginning of the second Heart Sound, T4. The output signals marking these times are connected to one shot multivibrators 34 and 35, the outputs of which are connected to processor 26 as signals C and D respectively. Heart Sound logic analyzer 32 is also connected to Heart Sound integrator 36 which is used to determine the energy content of the first and second heart sounds. The energy contained in the heart sound signals, and particularly the energy content of the first heart sound, is useful in determining the intensity of the mitral valve closure, which in turn is a reflection of the strength of contraction of left ventricle and is helpful in determining the index of contractility for the ventricle. Heart Sound integrator 36 is connected to multiplexer and A/D (analog to digital) converter which digitizes the energy data. Output, H, of A/D converter 37 is connected to processor 26 for analysis and storage. Synchronizing pulse, I, from A/D converter 37 is connected to processor 26 and signals when data is ready.

Control logic 38 shown connected between EKG logic analyzer 24 and Heart Sound Logic Analyzer 32 is used to provide synchronizing pulses to logic analyzer 32, integrator 36 and to carotid pulse slope detector 40 referenced to T0, the beginning of the QRS complex.

Figure 4:
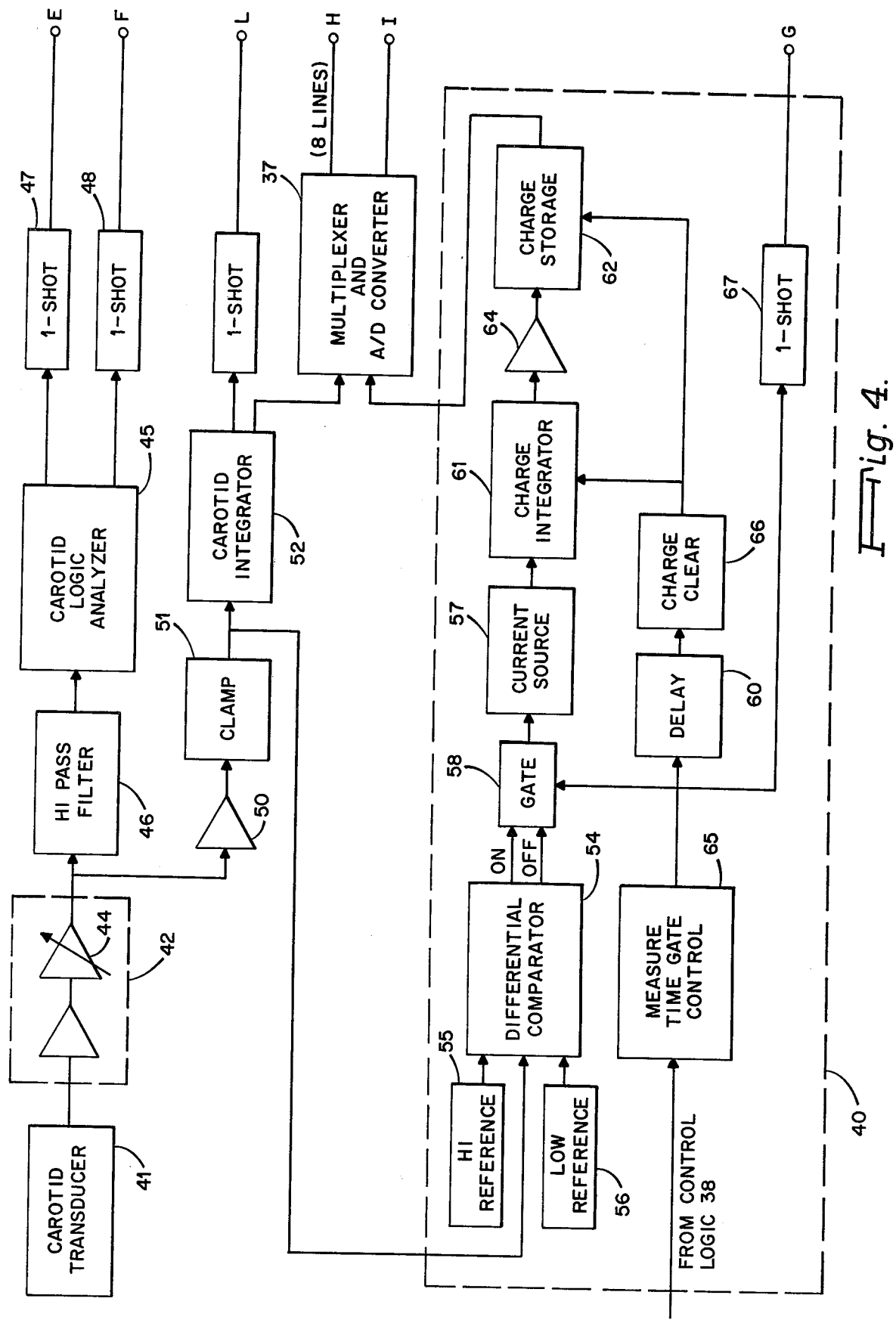
FIG. 4—Detailed block diagram of the carotid signal processor of FIG. 2.

Referring to FIGS. 2 and 4, the carotid signal is obtained by transducer 41 and connected to buffer amplifier 42 including variable (adjustable) gain amplifier 44. Amplifier 42 is connected to carotid logic analyzer 45. The signal is then passed through Hi pass filter 46. Hi pass filter 46 is designed to block low frequency artifacts. Carotid logic analyzer 45 consists of a network of gates and one-shots used to determine the time of the start of the Carotid pulse, T3, and the time of occurrence of the dichrotic notch, T5, relative to T0. The outputs of analyzer 45 are connected to one-shots 47 and 48, the outputs of which E and F are connected to processor 26. Additionally, the amplifier 42 is connected to buffer amplifier 50 and thence to clamp circuit 51 and carotid integrator 52. Integrator 52 is designed to determine the mean value of the carotid pulse. Integrator 52 is connected to multiplexer and A/D converter 37 for conversion to digital form. The output of multiplexer and A/D converter 37 is connected to processor 26 on signal lines H.

The output of clamp circuit 51 is also connected to carotid pulse slope detector 40 for slope determination. The operation of this circuit is better understood by referring to FIG. 4 which shows a detailed breakdown of the slope detector.

Referring to FIG. 4, clamp circuit 51 is connected to differential comparator 54 which compares the carotid signal to high reference voltage 55 and low reference voltage 56. The output of comparator 54 is connected to controlled current source 57 through gate 58. Current source 57 in turn is connected to charge integrator 61 which accumulates a voltage as a function of the time current source 57 is on. Charge integrator 61 is connected to charge storage 62 through buffer amplifier 64. The output charge storage 62 is connected to multiplexer and A/D converter 37.

Control Logic 38, as well as being connected to Heart Sound Logic Analyzer 32, is also connected to Heart Sound Integrator 36, Measure Time Gate Control 65 and Charge Storage 62. Measure Time Gate Control 65 is a timing circuit synchronized by Control Logic 38. The output of Measure Time Gate Control 65 is connected to Gate 58, Charge Clear 66 and One-Shot multivibrator 67. Gate 58 is an ON/OFF gate enabling the output of Comparator 54 to drive Current Source 57 during a timed interval. Charge Clear 66 is a discharge circuit operative to clear stored charge in Integrator 61 and Storage 62. Multivibrator 67 provides a synchronizing output G to Processor 26.

Transducers 20 are those conventionally used for electrocardiographs and sense electrical nerve signals in the body providing an amplified electrical output. Transducer 28 is suitably a bimorphic transducer responsive to vibrations such as caused by the opening and closing of the mitral and aortic valves. Again an electrical output is produced. Carotid transducer 41 is secured in a neck strap holding it firmly against the carotid artery. Transducer 41 is a pressure transducer registering flow changes in the artery by dilation and contraction of the artery and providing a corresponding electrical signal. A conventional sphygmomanometer, 70, with pressure gauge 71 is also utilized.

Data Processor 26 is suitably a dedicated computer or may be any of numerous general purpose computers. It has keyboard 72 for manual data entry, data display 74 and input connections for terminals A through L. All of terminals A through L except terminal H provide timing signals. Terminal H is actually a plurality of terminals connecting data from A/D Converter 37.

In operation, the diastolic and systolic pressures are obtained from meter 71 using pressure cuff 70 and entered into processor 26 by keyboard 72. Next, with all transducers 20, 28 and 41 in place and connected, carotid transducer 41 is normalized. This is performed by adjusting amplifier 44 to get a one volt peak-to-peak signal. This one volt then represents the full excursions between diastole and systole as depicted on curve 12 of FIG. 1.

Amplifier 50 amplifies this signal by an order of magnitude to give a 10 volt peak-to-peak signal which is then clamped at one peak as a reference by clamp 51. For example the signal can be clamped to zero volts at its bottom peak which can represent diastole. The amplified and clamped carotid signal now goes to Comparator 54. Low Reference 56 can be set at 0.1 volt and High Reference 55 can be set at 1.1 volt. Comparator 54 will then gate ON current source 56 as soon as the carotid signal at the input of Comparator 54 reaches 0.1 volt just beyond diastole (FIG. 1). Gate OFF will occur 11% of the way to systole while the slope is still nearly linear with the left ventricular pressure slope preceding diastole. Current Source 57, Charge Integrator 61 and Charge Storage 62 act as a timer. Current Source 57 is a constant current source and charges integrator 61 at a constant rate while the carotid signal at the output of amplifier 44 increases by 1.0 volt. Since the variation in the carotid signal has been established at a fixed value (by references 55 and 56) the carotid pulse slope time will always be inversely proportional to the charge integrated by Integrator 61. Stored charges are cleared each cardiac cycle so that updated slope time is always available. The charge representing slope time is provided to Multiplexer and A/D Converter 37 as a voltage from Charge Storage 62. A pulse from one-shot multivibrator 67 on terminal G and a synch signal on Terminal I tell Processor 26 that the slope time information is available on lines H. The slope time information on line H is used with diastolic and systolic pressure valves to obtain the carotid pulse slope adjacent diastole. As has been suggested above, carotid transducer 41 can be calibrated against diastolic and systolic cuff (sphygmomanometer) pressures to provide an electrical output directly corresponding to the carotid pressure wave. In that case the transducer output (before normalizing) would be fed directly to processor 26 in combination with the slope time information for obtaining carotid pulse slope.

Alternatively the systolic and diastolic pressures from the cuff can be entered by keyboard 72 to provide the basis for carotid pulse slope processing. Looking at FIG. 1 and assuming that Gate OFF for comparator 54 is established at one tenth of the way from diastole to systole, it will be seen that the carotid slope equals one tenth of the difference between systolic and diastolic pressure divided by the slope time (as provided on line H).

Diastolic pressure and carotid slope having been provided, only the times T2 and T3 are required for:

$$LVEDP = DIA - (T3 - T2)CS$$

T2 is the start of the first heart sound and is provided at terminal C by one-shot multivibrator 34. This signal is sorted out relative to the beginning of a QRS complex by Analyzer 32 synchronized by information from EKG Analyzer 24. In order to make sense from this Processor 26 requires time T0 also which is provided at terminal A by one-shot multivibrator 25.

T3 is the start of Aortic pressure pulse 16 and is sensed through carotid transducer 41 and made available to Processor 26 at terminal E by one-shot multivibrator 47. Logic Analyzer 45 sorts out the start of the aortic pulse from other variations such as dichrotic notch 75. No timing signal to analyzer 45 is necessary from EKG analyzer 24 since the aortic pulse start is distinctive and only occurs once in a cardiac cycle.

With minimal additions, the apparatus needed to derive LVEDP in accordance with the present invention, also provides massive additional helpful data.

The computer accepts the signals A through L, and processes, computes and stores the computed information as follows.

Signals A through F represent times for the various events occurring during the Cardiac cycle: (All times referred to T0).

T0—The start of the Cardiac Cycle at the beginning of the QRS complex.

T1—The end of the QRS complex (Also is QRS width).

T2—The start of the First Heart Sound (HS1).

T3—The start of Carotid Pulse upstroke (Also is Pre-ejection period, PEP).

T4—The start of Second Heart Sound.

T5—The occurrence of the Dichrotic Notch (Also PEP +LVET).

Signal H includes the first and second Heart Sound energy information, the Mean Carotid Pressure information and the Carotid Slope time information, all determined at different times during the Cardiac cycle. The computer is signalled that the A/D data is ready for entry by the appropriate one-shots (G, J, K, L) and accepts the data accordingly. The one-shots provide interrupt signals to the computer allowing time and A/D data to be entered and processed.

A computer program has been used providing for the averaging of 10 samples of each signal, each sample being within 20% of the previous. This is done to minimize errors due to artifacts that could distort the data and the resulting computations.

The program utilized was operated as a priority interrupt commonly used when multiple inputs and background computations are required for real time analysis of input data. Functionally the program was written to accept the input data as previously described, perform calculations, do averaging of the results and output the computed results to a variety of peripheral displays including printers, CRT's and digital readouts.

The data available for output from the computer and calculations performed by the computer to determine the important cardiac parameters are described below.

LVEDP—This has been described above.

Mean Arterial Pressure (MAP)—This parameter is computed using the equation:

MAP=DIA+Mean Carotid Pulse, where Mean Carotid Pulse is taken as the integral of the Carotid Pulse and is approximately equal to ⅓ (SYS−DIA).

Electromechanical Systole—The temporal occurrence of important events in the cardiac cycle. These times are determined by the logic analyzers and are fed to the computer for averaging and for use in computing certain other cardiac parameters such as LVEDP. These include:

R—R interval (T0—T0')—The time between two adjacent QRS complexes.

T2—The start of the first Heart Sound.
T3—The start of the Carotid Pulse.
T4—The start of the second Heart Sound.
T5—The occurrence of the dichrotic notch.

Additional temporal parameters are computed from the input data and include:

Heart rate (HR)—The reciprocal of R−R interval.
LVET (T6)—The ejection period of the left ventricle.
STI Ratio (T3/T6)—The ratio of PEP to LVET.

Other computed parameters:

In addition to the parameters already mentioned, the computer calculates certain other key indicators of cardiac activity.

Among these are:
Cardiac Output—C.O.
Systemic resistance—S.R.
Contractility Indes—C.I.
Stroke Volume—S.V.
Triple Product—T.P.

The determination of the value of these parameters requires a keyboard data input of the End Diastolic Volume (EDV) and the End Systolic Volume (ESV) of the patient's left ventricle as determined by ultra-sound or some other non invasive technique.

The apparatus as presently described may be used to determine other important cardiac information non invasively by simple modification of the program controlling the computations. This is readily apparent to those versed in the art of computer software.

Thus, while the invention has been described with respect to a specific embodiment and method, it has broad utility and it is contemplated to cover variations that are obvious and provide useful additional results.

I claim:

1. A method of obtaining LVEDP (left ventricular end diastolic pressure) in a mammalian body comprising:
   (a) measuring diastolic and systolic pressures;
   (b) detecting the start of the electrocardiograph QRS complex;
   (c) detecting the start of the first carotid pulse after the start of said QRS complex;
   (d) detecting the start of the first heart sound after the start of said QRS complex;
   (e) determining the carotid pulse slope by:
      (1) sensing the carotid artery pressure by a transducer secured against the neck;
      (2) converting the pressure variations sensed to electrical voltage signals;
      (3) amplifying said voltage signals;
      (4) adjusting the amount of said amplifying to calibrate the swing of said voltage signals to a predetermined level;
      (5) processing said signals as amplified to obtain carotid pulse slope time by the time it takes said voltage signals to pass between two fixed reference levels;
      (6) processing said carotid pulse slope time with said diastolic and systolic pressures to obtain carotid pulse slope; and,
   (f) calculating LVEDP by processing the equation:

$$LVEDP = DIA - (T3 - T2)CS$$

Where:
DIA=diastolic pressure at a brachial artery
T3=Time from start of QRS complex to start of carotid pulse
T2=Time from start of QRS complex to start of first heart sound
CS=Carotid pulse slope.

2. A method of obtaining LVEDP according to claim 1 wherein diastolic pressure is measured with a sphygomomanometer, the start of the QRS complex is analyzed from an electrocardiograph waveform sensed by noninvasive electrocardiograph electrodes, and both the start of the carotid pulse and the carotid pulse slope are analyzed from the signal of a carotid artery transducer applied noninvasively to the neck.

3. A method of obtaining LVEDP according to claim 1 wherein the electrocardiograph signals, the heart sound signals, and the carotid pulse signals are processed electronically and provided at electrical input terminals of a computer and the diastolic pressure from a sphygmomanometer is provided manually by a keyboard to said computer.

4. A method of obtaining LVEDP according to claim 1 wherein the carotid pulse slope is analyzed by measuring the time taken for the carotid pulse pressure to pass a predetermined small fraction of the pressure rise between diastole and systole.

5. A method of obtaining LVEDP according to claim 4 wherein said predetermined small fraction commences adjacent to diastole and is no greater than one tenth of the pressure rise between diastole and systole.

6. Apparatus for obtaining LVEDP (Left Ventricle End Diastolic Pressure) noninvasivety comprising:
   (a) A sphygmomanometer;
   (b) at least two electrocardiograph transducers;
   (c) a heart sound transducer;
   (d) a carotid pressure transducer providing an electrical output signal and means for securing it against a mammalian neck;
   (e) a first electronic processor connected to said carotid pressure transducer and comprising:
      (1) an adjustable gain amplifier connected to receive said electrical ouput signal;
      (2) means to supply two predetermined reference voltages;
      (3) a comparator for comparing the output of said amplifier to said reference voltages;

(4) electrical circuit means connected to said comparator and providing an output signal related to the time taken by a signal from said amplifier to change level by the difference between said two predetermined voltages in order to provide a carotid pulse slope time;

(f) additional electronic processors connected to the output of said electrocardiograph transducers and said heart sound transducer; and, (g) a data processor connected to receive data from each of said electronic processors and having a data entry terminal for receiving data obtained by said sphygmomanometer, said data processor being programmed to obtain LVEDP in accordance with the equation:

$$LVEDP = DIA - (T3 - T2)CS$$

Where:
DIA = Diastolic Pressure
T3 = Time from start of QRS complex to start of carotid pulse upstroke
T2 = Time from start of QRS complex to start of first heart sound
CS = The pressure time slope of the carotid pulse at the beginning of the upstroke.

7. Apparatus for obtaining LVEDP according to claim 6 wherein said carotid pulse transducer generates an electrical signal proportional to carotid pulse amplitude and the electronic processor connected to said carotid pulse transducer comprises a constant current source, a charge integrator connected to the output of said constant current source and means to gate said constant current source ON between two fixed reference levels of said electrical signal whereby said charge integrator accumulates a charge that is a function of the slope of the carotid pulse.

8. Apparatus for obtaining LVEDP according to claim 7 wherein said electronic processor connected to said carotid pulse transducer furter comprises an analog-to-digital converter connecting the output of said charge integrator to said data processor.

9. Apparatus for obtaining LVEDP according to claim 6 wherein each of said electronic processors comprises means to analyze specific reference variation points in the waveforms from the respective transducers and one-shot multivibrator means connected between said means to analyze and said data processor so as to provide pulses to said data processor representative of each of said reference variation points to establish time references in a cardiac cycle.

* * * * *